(12) United States Patent
Fox et al.

(10) Patent No.: US 7,970,554 B2
(45) Date of Patent: Jun. 28, 2011

(54) METHOD AND DEVICE FOR SECURELY STORING DATA

(75) Inventors: Michael J. Fox, Glencoe, OK (US);
Craig A. Aker, Stillwater, OK (US);
Matthew Dock, Stillwater, OK (US);
Steven M. Trost, Stillwater, OK (US)

(73) Assignee: Engius, LLC, Stillwater, OK (US)

( * ) Notice: Subject to any disclaimer, the term of this patent is extended or adjusted under 35 U.S.C. 154(b) by 0 days.

(21) Appl. No.: 12/651,039

(22) Filed: Dec. 31, 2009

(65) Prior Publication Data

US 2010/0324835 A1    Dec. 23, 2010

Related U.S. Application Data

(60) Continuation of application No. 11/875,501, filed on Oct. 19, 2007, now Pat. No. 7,668,666, which is a division of application No. 11/054,565, filed on Feb. 9, 2005, now Pat. No. 7,286,944, which is a division of application No. 10/351,856, filed on Jan. 24, 2003, now Pat. No. 6,865,515.

(60) Provisional application No. 60/351,393, filed on Jan. 24, 2002, provisional application No. 60/391,471, filed on Jun. 24, 2002.

(51) Int. Cl.
*G06F 11/30* (2006.01)

(52) U.S. Cl. .......................................................... 702/33
(58) Field of Classification Search .................... 702/33, 702/182–185, 188
See application file for complete search history.

(56) References Cited

U.S. PATENT DOCUMENTS

2006/0170535 A1 *  8/2006  Watters et al. ............. 340/10.41
\* cited by examiner

*Primary Examiner* — Edward Raymond
(74) *Attorney, Agent, or Firm* — Dunlap Codding, P.C.

(57) ABSTRACT

A system for providing secure access to mechanical data associated with the mechanical properties of a concrete mass. The system includes a logger associated with the concrete mass and having at least one sensor adapted to measure physical properties of the concrete mass and generate sensor data indicative of the physical properties of the concrete mass. The logger also has a microprocessor adapted to receive the sensor data and calculate mechanical data associated with the concrete mass and an outbound data transfer device. The system includes a reader adapted to receive the mechanical data associated with the concrete mass from the outbound data transfer device of the logger. Lastly, the system includes a computer receiving the mechanical data from the reader and distributing the mechanical data to one or more users via the Internet, a world-wide network of information sharing computers, or using the world-wide web.

30 Claims, 10 Drawing Sheets

METHOD AND DEVICE FOR SECURELY STORING DATA

CROSS-REFERENCE TO RELATED APPLICATIONS

The present application is a continuation of U.S. Ser. No. 11/875,501, filed on Oct. 19, 2007 now U.S. Pat. No. 7,668,666; which is a divisional of U.S. Ser. No. 11/054,565, filed on Feb. 9, 2005, now U.S. Pat. No. 7,286,944; which is a divisional of U.S. Ser. No. 10/351,856, filed on Jan. 24, 2003, now U.S. Pat. No. 6,865,515 which claims priority to the provisional patent application identified by U.S. Ser. No. 60/351,393, filed on Jan. 24, 2002. The present application also claims priority to U.S. Ser. No. 60/391,471, filed on Jun. 24, 2002. The contents of all of the referenced patent applications are incorporated by reference herein in their entirety.

BACKGROUND OF THE INVENTION

The present invention generally relates to methods and devices for securely storing data within a protected environment. Specific embodiments of the invention include recording time-stamped activity data, storing temperature data within the protected environs of a concrete mass, and secure calculation and storage of data relating to the properties of a concrete mass and, more specifically, mechanical strength data of the concrete throughout its curing process.

Today, there are secure "boxes" that are manufactured and sold to the government for data communication across telephone lines. Drawbacks of the secure boxes are that they are large and not secure in the particular environment that they are used in. In other words, the boxes may be capable of creating, sending, and receiving data that is secure, but the box itself may not be secure.

The personal computer industry offers software and personal computers that create, send, and receive secure data. The software operates in conjunction with a generic computer. Again, the data that are sent or received are secure, but the computers are not secure.

Two options are available for making the data and the hardware secure. The first is to make the hardware small enough to be carried from place to place, so that one can personally guard against its loss or unauthorized use. However, this alternative is impractical if the data need to be available and accessible to various other parties, and the data remain susceptible to loss or misplacement. As such, a second alternative is hereby disclosed, wherein the hardware and, subsequently, the data, are secure protected within an immovable mass. The present invention provides a method and device for securing the hardware and, subsequently, securing the data stored therein, from loss due to theft, misplacement, tampering, and the like, yet keeping the data readily accessible to any authorized personnel who may have need to access the data.

Concerning the construction industry, data of all sorts are vital to construction projects of all kinds. As the information age and the construction industry collide, the availability of construction-related data for future planning and analysis is paramount. Furthermore, the validity of the data is, in many instances, as important as or at times even more important than the data themselves. The preferred embodiment of present invention relates to the protection of crucial data for use within various industries, such as the construction industry, financial industries, medical industries, and any other industries needed open access to securely-protected data, as well as the secure transference of the data to their intended recipients.

HOME-BUILDING EXAMPLE

By way of example, home builders have a need for keeping track of which sub-contractors are working at each of their construction sites and/or keeping track of which of their own workers are at work, where they are working, and what work activities they are performing throughout the construction of the house (thus functioning as an inexpensive on-site time-clock for workers, subcontractors, etc.). To track and manage this data, home builders need a system to receive, store and, when needed, transfer the data to its intended recipient—all with the utmost of integrity and validity (i.e. without potential for tampering or loss of data along the way). One embodiment of the present invention provides the functionality required to meet this need.

CONCRETE CONSTRUCTION EXAMPLE

Another embodiment of the present invention relates to the protected calculation and storage of concrete maturity and concrete strength data. In the construction field today, concrete is one of the most widely used construction materials. One method for determining the mechanical strength of a mass of concrete is the "maturity method." In the maturity method, one maintains a record of the internal temperature history of the concrete mass as it cures. Curing is the strengthening of the concrete through the process of hydration that occurs over a number of days. When concrete stays moist, the moisture allows the chemical reaction between the cementitious materials and water to continue. From the curing temperature history, one can determine the mechanical strength from previously-determined empirical equations. For these equations to be valid, one needs to determine coefficients for these equations that correspond to a given concrete mix design. For a different mix of concrete, the coefficients have to be recalculated. In this sense, the equations are "calibrated" according to the specific mix of concrete to be analyzed.

The term concrete is generally used in the construction industry to refer to a mixture of Portland cement or other cementitious or pozzolanic materials, coarse aggregate such as gravel, fine aggregate such as sand, water and various chemical admixtures which, upon hydration of the cementitious and pozzolanic materials, becomes a hardened mass. As used herein, the term concrete refers to concrete as it is commonly defined in the construction industry and to formed cement, which is cement and water that hardens into a solid mass upon hydration.

The term concrete mass is defined herein to be a mass or body which is made from concrete, mortar, cement, or the like. This definition is in contrast to the term concrete form which, when used herein, refers to the structures into which concrete is poured to produce a concrete shape that holds its shape upon hardening.

One embodiment of the present invention provides a means for calculating and storing the maturity and/or strength data within a protected environ and, subsequently, to transfer the data to its intended recipient without risk of loss or alteration of the data at any point (it should be noted that in the provisional application identified by U.S. Ser. No. 60/351,393, it is mistakenly stated that the prior art loggers store maturity data. To Applicant's knowledge no one prior to Applicant has stored maturity data in a logger.). Although there are existing devices and methods for non-destructive testing of concrete masses using the maturity method, further improvements are sought to shorten construction schedules, promote safety and to thereby save money. It is to such improvements in the devices and methods used in the maturity method that the present invention is directed.

DETAILED DESCRIPTION OF THE PREFERRED EMBODIMENTS

Figure 1:
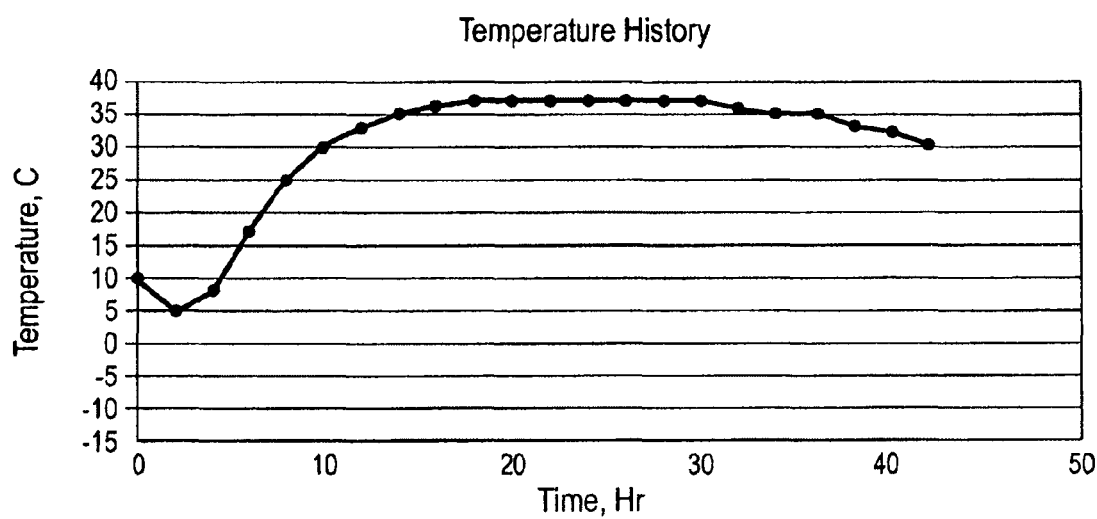
FIG. 1 is a graph of the temperature of a typical concrete mass as a function of time while the concrete mass is curing.

The preferred embodiment of the present invention comprises an apparatus (hereinafter referred to as a "logger") which is capable of receiving sensor and/or non-sensor data, storing said data, and later transferring said data to a separate apparatus. Sensor data are received via communication with a sensor (wherein said sensor may be hard-wired and, as such, contained within the logger itself or may be separate with a communication link between the sensor and the logger). Non-sensor data are received via communication with a user. Communication with the user can be in real-time, wherein the user directly loads data into the logger via a communication interface. By contrast, communication with the user can be via pre-initiated and/or delayed interactions. For instance, the user may pre-load certain data in the logger prior to its placement on the job site. Similarly, the user may pre-load certain sets of data into a handheld apparatus (hereinafter referred to as a "reader") wherein later, the user can select from those pre-loaded data sets to determine which data set is applicable and, in so choosing, instruct the reader to load that specific set of pre-loaded data into the logger.

The logger is preferably configured such that it can be securely anchored in a given location. The preferred anchoring means involves embedment or attachment of the logger into or onto an immovable (or difficult-to-move) object, such as a concrete mass. If a concrete mass is utilized as the anchoring means, the concrete mass could be a concrete slab of a building, a concrete column on a bridge, a concrete pavement, a concrete vault wall, or any number of other uses of concrete. The logger can be embedded into the concrete by placing it into the concrete forms just prior to placement of the concrete itself, or the logger can be physically placed into the concrete mass while the concrete remains in its plastic (non-hardened) state. Alternatively, the logger can be permanently attached such as via a welded-encasement to or within a metal wall, a steel I-beam or other difficult-to-move object. Similarly, the logger can be stored within a vault or other protective means, with the communication interface (e.g. wires, or RF transmission) accessible from outside the vault.

Another embodiment of the present invention includes an apparatus and method for measuring and recording the internal temperature history of a concrete mass. Given the curing temperature history, one can calculate and record the mechanical strength of the concrete mass. The apparatus for measuring and recording the curing temperature history includes a logger embedded within the concrete mass and a reader located outside the concrete mass.

For this embodiment, the logger includes at least one temperature sensor, a first memory device, a microprocessor and a power source. The first memory device may be one of several memory devices, such as a random access memory device within a computer, flash memory or an electrically erasable programmable read-only memory (EEPROM). The logger is embedded in the concrete either before or immediately after the concrete is poured. Within the logger, the sensor is connected to the microprocessor. The temperature sensor is typically a thermistor for which the electrical resistance changes in an electrical circuit based on the changes of temperature sensed. The temperature sensor sends temperature-dependent data signals to the microprocessor for processing. The microprocessor receives the data signals and calculates a variable known as "maturity." The maturity value is a representation of the degree of cementitious hydration that has occurred within the concrete mass. Several different "functions" are available for calculating maturity. The two most common maturity functions are the Nurse-Saul method and the Arrhenius method. The calculations for these methods are discussed at length in a publication by the American Society for Testing and Materials (ASTM) entitled *Standard Practice for Estimating Concrete Strength be the Maturity Method* (ASTM C 1074), the content of which is hereby expressly incorporated by reference. The Nurse-Saul maturity is defined to be the area under the curve when the internal concrete temperature is plotted against time. This can be expressed by the equation:

$$M = \sum_0^t [(T - T_o) \cdot \Delta t]$$

where
M=concrete maturity expressed as temperature-time factor (TTF) (in ° C.-Hours)
T=average temperature (in ° C.) during time interval $\Delta t$.
$T_o$=datum temperature (in ° C.)
$\Delta t$=length of time interval (in hours)
The Arrhenius maturity is defined as an equivalent age. This can be calculated by the following equation:

$$M = \sum_0^t \left[ e^{-\frac{E_a}{R} \cdot \left(\frac{1}{T+273} - \frac{1}{T_r+273}\right)} \cdot \Delta t \right]$$

M=concrete maturity expressed as equivalent age (in hours or days)
$E_a$=apparent activation energy (in J/mole)
R=universal gas constant (=8.3144 J/mole/K)
T=average temperature (in ° C.) during time interval $\Delta t$.
$T_r$=reference temperature (in ° C.)
$\Delta t$=length of time interval (in hours or days)

The maturity variable is then used to calculate the mechanical strength of the concrete. The calculation of mechanical strength from maturity is typically based upon a pre-determined empirical relationship between maturity and mechanical strength for the specific concrete mix design for which strength determinations are desired. The conversion of maturity data to strength data can occur within the handheld reader or within the logger itself. Whenever strength calculations are to be performed within the logger, the empirical data relating maturity to strength will have been loaded into the logger.

The microprocessor is preprogrammed with a set of instructions for controlling the frequency of sensor readings, determining how to use the sensor readings, determining which maturity function to use when calculating maturity, and determining how to communicate with external devices such as the reader. The microprocessor is designed to calculate the maturity in real-time based on one of the maturity methods referenced above or any other suitable method.

One advantage of the preferred embodiment of the present invention is that a user can store within the first memory device strength-maturity relationship information in the form of individual points of a calibration curve and/or coefficients for various types of calibration equations. These equations may be various types of curve-fitting equations used to approximate the calibration curve. Using this information, the microprocessor can calculate mechanical strength in real-time within the safe confines of the concrete mass. The ability of a preferred embodiment of the present invention to determine maturity and strength within the concrete mass has several benefits.

A first benefit of calculating the maturity and strength within the concrete mass is that workers can read mechanical strength directly in units of pressure (e.g. pounds per square inch, psi, or megaPascals, mPa) without the need for conversion tables or separate calculation devices. A second benefit is that the microprocessor may be coupled with an indicating device to indicate the concrete has attained a certain level of mechanical strength.

The device that indicates that the concrete has attained a certain level of mechanical strength can be an embedded or external radio frequency (RF) transmitter that sends a radio signal. Another type of indicator can be a visual indicator such as a series of lights (e.g. four light-emitting-diodes, each perhaps having a different color than the rest) that indicate when the concrete has attained a given threshold mechanical strength level (e.g. 25%, 50%, 75% and 100% of the design strength).

The first memory device is controlled by the microprocessor and stores temperature data, maturity data, and mechanical strength data (collectively referred to herein as mechanical data) at predetermined time intervals in order to record the time, maturity and mechanical strength history. The time histories of maximum and minimum temperatures are also stored in the first memory device. Furthermore, desired threshold levels for temperatures, maturity and mechanical strength (mechanical properties) at various times can be stored in the first memory device. Whenever one reaches the desired threshold levels, the elapsed time to reach these threshold levels is recorded in the first memory device.

One may use the reader to observe the values of the mechanical properties during the hardening process or after the concrete mass has hardened. The reader connects to the microprocessor via a connection. The reader may be a proprietary hardware/software device. Preferred embodiments for the reader include a hand-held reader, a palm-sized computer, a laptop computer, and a desktop computer. The reader is also referred to herein as an external device. The connection between the microprocessor and the reader can be made using a RF communication interface, a one-wire (plus ground) communication interface, a coaxial cable interface, an optical (fiber-optic) communication interface, an inductive wire (loop) communication interface, or an inductive RF communication interface. The use of a coaxial cable interface provides significant advantages in that the communication signal is not impeded by the electromagnetic properties of the surrounding medium. This enables substantial increases in communication throughput speeds.

The communication interface between the microprocessor and the reader uses self-detection algorithms to detect any transmission errors. For example, when data are sent from the microprocessor to the reader, the data is organized into packets of bytes and these packets have a one-byte checksum value. This checksum value is a simple addition of all of the other bytes in the packet. This algorithm allows the reader to add up the bytes received and determine whether this sum matches the checksum byte sent with the packet. If the sum does not match the checksum byte, there has been a transmission error. This algorithm is used when the preferred embodiment is communicating with a separate computer. This algorithm catches all one-bit transmission errors and most multi-bit errors.

Another advantage of a preferred embodiment of the present invention is that the first memory device, the microprocessor, the temperature sensor, and battery are relatively inexpensive, commonly available devices. Furthermore, with the logger completely embedded in an immovable mass, the logger and the data it contains are not subject to damage due to theft, environmental exposure or other hazards.

Yet another advantage of the preferred embodiment of the present invention is that the reader is removably connected to the microprocessor of the logger. As such, the data is available to authorized users at their convenience. In addition, data from the first memory device can be uploaded to the reader for secured transference to other authorized personnel through the use of encryption and decryption software. Any suitable encryption/decryption method may be used. Thus, a contractor who installs the logger can control access to those who are authorized to view the data. Furthermore, with the raw data encased in the concrete mass, the data can not be altered. Thus, true histories of the mechanical properties are ensured. When the reader is embodied as a laptop, palm-sized or desktop computer (collectively, a computer) proprietary software or hardware on or connected to the reader stores the encoded computer file directly on the reader without the use of an intermediate hand-held device.

Another great advantage of the preferred embodiment of the present invention is that, at the convenience of the user, the reader is connected to the microprocessor and memory means, and the information from the memory means (i.e. current and/or historical temperature, maturity and/or strength) can be displayed at any time the reader is connected. Furthermore, the data from the memory means can be up loaded to the reader for secure transference to other interested parties. This part of the invention involves a method of data transmission which securely conveys recorded data to and by means of the reader. In essence, the method involves the secure transference of the data from the memory means to an intended recipient without susceptibility to alteration from any user along the way. The initial recording of the data to the memory means is controlled by the internal programming of the microprocessor and, as such, is not alterable by any users. The reader is then used to retrieve the recorded data from the microprocessor and memory means. Again, the retrieval and recording of the data is controlled by the internal programming of and/or proprietary software installed on the reader and, as such, is not alterable by the user. In the preferred embodiment, the reader (a proprietary handheld device) is connected to a personal or palm computer and then transmits the recorded data to the computer as binary data with subsequent encoding so as to make it unalterable without the required decoding key. If the reader is embodied as a laptop, personal or palm computer, proprietary software and/or hardware installed on and/or connected to the reader will store the encoded computer file directly on the reader without the use of an intermediate handheld device.

Once stored onto a laptop, personal and/or palm computer, the encoded computer file can then be copied and distributed at will, but remains free from alterations by the users due to the proprietary encryption algorithms employed. A separate software program capable of reading, but not altering, the data in the encoded computer file is then used to view the data and subsequently copy the data into an alterable form for use in a word processor, spreadsheet or other program or device for subsequent printing, editing, graphing, etc.

Thus, a construction project worker can embed, at various locations, the loggers (each consisting of a temperature sensor, memory means, microprocessor and battery) within concrete masses, and at some later date, a worker connects a reader to the microprocessor and memory means, up loads the data, then downloads the data in a secure file format into a laptop, personal or palm computer. Thus, a construction operation needs only one reader for viewing and transferring the temperature, maturity and/or strength data from multiple locations within multiple concrete structures and even at multiple sites.

Additionally, the loggers may be embedded within precast components, which are typically cast at a remote site and then transported to the construction site. In such event, continuous monitoring and recording of temperature, maturity and/or strength during transport or curing is available. Upon arrival at the construction site, the microprocessor and memory means are accessed via the reader and viewed and/or securely transferred to a laptop, personal or palm computer. This enables timely evaluation of the sufficiency of the concrete strength prior to subsequent loading and/or post-tensioning operations.

Once the encrypted computer file is stored on the computer, the encrypted information can be copied and distributed, but it cannot be altered by the user because of the encryption algorithm. A separate software program capable of reading, but not altering, the data in the encoded computer file is then used to view the data and to subsequently copy the data into an alterable form for use in a word processor, spreadsheet, or other program or device.

With the configuration described above, a construction worker can embed the loggers at various locations within the concrete mass and at a later date connect a reader to the microprocessor and the first memory device. Then, the worker can transfer the data in a secure file format to the computer. Thus, the construction worker needs only one reader for viewing and transferring the data from multiple locations within multiple concrete structures at multiple sites.

An additional advantage of the preferred embodiment described above is that unskilled personnel can be trained to initiate the recording and calculating functions of the logger and to collect and transfer the mechanical data.

The loggers may be embedded in a concrete mass in a number of ways. One method is to implant loggers into the concrete mass as the concrete mass is being poured or just after the concrete mass is poured. These embedded loggers are spaced along a length or width of a concrete mass and at different depths within the concrete mass. The loggers may also be pre-placed within the concrete mass by attaching the loggers to reinforcing steel or concrete forms.

Other sensors or probes may be used in addition to the system of the preferred embodiment to generate data for monitoring strength gain or other desired characteristics of the hardened concrete mass. Suitable sensors for use in conjunction with the preferred embodiment of the present invention are sensors to measure moisture, relative humidity, electrical conductivity, pH (acidity or alkalinity level). Other sensors may include ion selective sensors, thermal conductivity sensors, oxidation-reduction potential sensors and acoustic velocity sensors.

The logger itself uses several methods to perform its normal and proper function. One of these methods is that the logger performs self-testing to verify proper functioning. These self-tests include battery life tests, memory tests, and thermistor functionality tests.

Another method preferably performed by the logger is that the logger performs ratiometric temperature conversion, rather than temperature conversion using raw voltage data, to ensure accurate temperature measurement irrespective of input voltage. Ratiometric measurement is a measurement technique where an external signal is used to provide a voltage reference for a dual-slope analog-to-digital (A/D/) converter. The A/D converter is used to convert an analog signal such as voltage or current to a digital data signal. The external signal can be derived from a voltage excitation applied to a bridge circuit or pick-off supply, thereby eliminating errors due to power supply fluctuations.

The logger desirably uses data from a data look-up table to linearize temperature output from the thermistor. The use of the data look-up table eliminates non-linearity and thereby increases accuracy of the temperature measurement system. When performing difficult calculations, such as with the exponential Arrhenius maturity function, the logger desirably uses data from a data look-up table for calculating the function so that the calculation merely depends on the concrete temperature with simple multiplication of division, without the need for complex calculations using exponents or logarithms.

The logger desirably switches the thermistor sensor off between successive power readings to conserve battery power.

The logger is also desirably programmed to activate or begin reading mechanical data based on a number of different conditions. These conditions include a command from the reader, a change in communication wires, a sudden temperature change, a change in the temperature gradient through the concrete mass, an acoustic or magnetic signal from an external source, a radio or microwave signal, and a sonic pulse. The logger can also be programmed to activate when there is a change in the conductivity, pH, relative humidity, moisture content, density, hydrostatic pressure, viscosity, or penetration resistance of the concrete. The logger can also be programmed to activate when there is a specified time delay following any of the above-listed actions.

The logger desirably contains a "type of logger" byte which indicates the model of the logger. The type of logger byte enables the logger to check for compatibility and facilitates unique communication with the reader irrespective the logger type. This feature allows for the use of different types of loggers and allows revisions of logger types to be interrogated by a single reader.

The logger desirably uses higher sampling frequencies early in the hardening phase of the concrete mass when a strength gain curve is steepest. After the hardening phase, when the strength gain curve levels off, the logger uses a lower sampling frequency.

The logger desirably utilizes electrostatic discharge (ESD) protection on a communication bus to prevent electrostatic discharges from damaging the electronics.

The logger desirably uses one-wire (ground plus signal) digital communications to communicate.

The logger desirably contains a unique electronic serial number to facilitate subsequent identification for data transference. The use of the serial number enables features such as automatic data identification. Thus, as data are periodically read and transferred from the logger, corresponding database entries can be automatically identified and updated.

The logger is desirably enveloped in an encasement to protect the logger from hazards of the environment into which it may be placed (e.g. a hydrating concrete mass). The encasement can be an elastic or elastomeric encasement or a hardened encasement. For a hardened encasement, a dual-stage encasement is preferable, wherein the first-stage encasement ensures that all logger components are separated from the outside of the second-stage hardened encasement (and, subsequently, also separated from the medium of the external environment) by a minimum distance. This separation is accomplished by the location of tabs on the first-stage encasement, a conical-shaped bottom to said first-stage encasement, and by requiring that no components extend into any of the tabs or the tip of the conical bottom during the first-stage encasement process. The hardened encasement can be epoxy resin, polyester resin, or any other suitable materials having sufficient characteristic and sufficient thickness to protect the logger components from effects of the medium and/or environment surrounding the logger. For an effective encasement, the thickness of said encasement must be adequate to shield electromagnetic interferences which can effectively "short out" the electrical signals within the logger resulting from uncontrolled capacitive coupling.

The loggers desirably use color-coded encasements or other visual differentiation features for easy identification of logger types and versions. Each of several colors corresponds to the logger type and version.

The logger desirably uses a temperature sensor located near the surface of the hardened encasement to minimize thermal lag times. This is important to provide accuracy to the temperature history.

The logger desirably receives as input from the user via the reader and stores in the first memory device additional information about the concrete mass. This information includes air content, water-to cementitious-materials ratio, unit weight, concrete slump, mechanical strength-maturity relationship curve data, datum or reference temperature, apparent activation energy, etc.

The logger desirably calculates strength in real time using the strength-maturity relationship data stored in the first memory device. The conversion of maturity to strength occurs within the logger without external interaction. Loggers of the existing art only store temperature data, which must be converted to maturity and then strength data by a separate, external computational device. An alternative approach is to upload temperature data to an external device which can be pre-loaded with calibration and then process the data as needed. By storing the calibration data within the logger, strength data can be accessed, viewed and uploaded by any reader, regardless of whether the reader has calibration data stored within the reader. A tremendous advantage results from the calculation of maturity and/or strength directly within the concrete mass in that integration intervals for the maturity calculations can be reduced practically without bounds (e.g. integration can occur once every second or even less). This advantage becomes possible because the logger need not store massive amounts of temperature data. Each time a new temperature measurement is taken and the subsequent maturity value and/or strength value is recalculated (i.e. updated), that temperature reading can be discarded, thus limiting the upside memory requirements for the logger.

Examples of calibration data are: $M_1$, $S_1$, $M_2$, $S_2$, $M_3$, $S_3$ . . . $D_1$, $D_2$, $D_3$, where M is the maturity, S is the strength and D could be additional useful data for enhanced maturity methods. The data correspond to particular time intervals at which the data is sampled. A simple maturity-to-strength conversion algorithm for producing a continuous curve would be to linearly interpolate between data points. A slightly more complex conversion algorithm is to linearly interpolate between log (M/S) data points. The use of point-to-point linear interpolation using a logarithmic transformation of maturity and strength values provides an accurate and true relationship of strength to maturity, yet preserves the concave nature inherent in the strength-maturity relationship curves even though the interpolation is linear.

The loggers desirably receive and store additional information about the concrete mass including user: (1) defined data location identifier; (2) latitude, longitude and elevation via a global positioning system; and (3) start-time synchronized to an atomic clock.

When communication wires are utilized with the logger, the logger of desirably uses color-coded communication wires to facilitate quick and proper attachment to the reader and also uses large-diameter communication wire for increased durability. The logger also uses connector-less connections to connect the communication wires to the logger rather than typical metal or plastic connectors, because the typical connectors are easily damaged. The connections are similar to speaker wire connections which consist of stripped wires that are tinned. The connections connect to a "crimp" style connector on the reader. This type of connection facilitates easy extension of communication wires in the field. The wire ends are tinned (plated with tin) to facilitate easy quick and problem-free attachment of the wires to the reader.

The logger also desirably uses a Z-bend wire configuration when the logger is connected to the reader by communication wires to relieve stress concentrations and thus effectuate proper sealing between the wires and the hardened encasement. The Z-bend wire configuration also protects the microprocessor from ion intrusion. For the Z-bend wire, the communication wire is routed under the battery to conserve space and to help maintain orientation of the wire during encasement operations.

The logger desirably uses universally expandable communication wire, when the logger uses a communication wire, to allow easy extension of the wire up to approximately 100 feet (30.5 m) in the field using common splicing techniques and equipment. This in turn enables easy remote access to the data. In addition, the logger uses a communication interface such that the communication wire can extend beyond 100 feet (30.5 m) (up to 1,000 feet (305 m) and beyond) with the inclusion of an in-line trans-impedance box or line driver.

The logger desirably uses graduated marks on the communication wires to indicate a logger depth of immersion in the concrete. These marks assist in proper placing of the sensors within the loggers with respect to the concrete mass.

The logger desirably predicts and provides a warning signal to the external device whenever damage to the concrete is anticipated due to excessive internal temperatures or freezing temperatures. The logger also provides a signal to the external device whenever a local threshold temperature or a minimum or maximum temperature has been reached. The logger also provides a signal to the external device to indicate the proper functioning and continued operation of the logger. The logger also predicts the time at which the threshold strength value is anticipated.

The logger, in certain embodiments, uses a serial data link which requires very low power for communication. For these embodiments, the logger can be activated by the serial link. The logger remains in a dormant standby or sleep mode until "awakened" by the reader. When connected, the reader pulls a data line "hi" to awaken the logger from the sleep mode. The logger can then receive commands. If commands are not received before a short timeout period, the logger returns to the sleep mode. Data is transmitted from the logger via an open collector 2-wire interface which requires very little power from the logger because the power for communications is provided by the reader.

The reader desirably synchronizes with the atomic clock (when so equipped) via an internet connection or Global Positioning System (GPS) receiver to store reliable and secure time-of-start information in the first memory device of the logger. The reader also stores global positioning system (when so equipped) location information in the first memory device of the logger. The reader also stores previous values of user-defined data inputs such as mix design information, datum or reference temperature, activation energy, threshold values in order to minimize the required number of inputs from the user when activating subsequent loggers. The reader also graphically displays maturity information.

The reader desirably uses dual-use function keys to enable additional functionality with a limited number of available keys. In other preferred embodiments, the reader continuously updates and displays current values of the mechanical data after a preset time has elapsed as long as the reader remains continuously connected to a logger. The reader shuts off after a preset time has elapsed without any user input and without continuous connection to a logger.

In general, temperature measurements with the logger and reader can be made traceable by the (National Institute of Standards and Technology). A special data-logging reader may be connected to each logger to provide continuous logging of mechanical data. Filenames of the data files during the creation of the secure and alterable electronic data files are based upon the serial numbers (and elapsed time at time of download from the logger) of the individual loggers from which the data were retrieved.

Another aspect of the invention is to immerse the loggers in an electrolytic test bath, such as sodium-chloride, to simulate the harshness of the concrete environment prior to using the logger in the concrete mass. The loggers are tested in the test bath to determine if water is able to directly infiltrate to the electronics or if undesirable electrical properties induced by an electrolytic external medium will negatively affect the proper function of the logger. Negative test results can be overcome by correcting any infiltration problems (i.e. leaks) and/or increasing the thickness of the protective encasement and/or changing the material properties of the encasement. For instance, a conductive material can be intermixed with the resin used for the second-stage hardened encasement. Alternatively, a metallic paint can be applied to the outside of the encasement, regardless of whether the encasement is elastic or hardened, thus providing the needed shielding from parasitic capacitance and other electromagnetic interferences.

In one embodiment, there is communication between the loggers and a central receiving logger periodically collects and stores data from other loggers within a certain distance. The data from the receiving logger is then transferred via the reader and published to the internet for viewing, downloading or analysis from anywhere in the world.

Description of the Figures

FIG. 1 is a typical time versus temperature plot for a concrete mass during the curing of the concrete. As shown in FIG. 1, the temperature of the concrete may drop for the first hour or so after it is set in place. Then, between about 2 hours and 20 hours, the concrete temperature rises to a maximum. From about 20 hours to about 30 hours, the temperature remains constant. After about 30 hours, the temperature slightly decreases.

Figure 2:
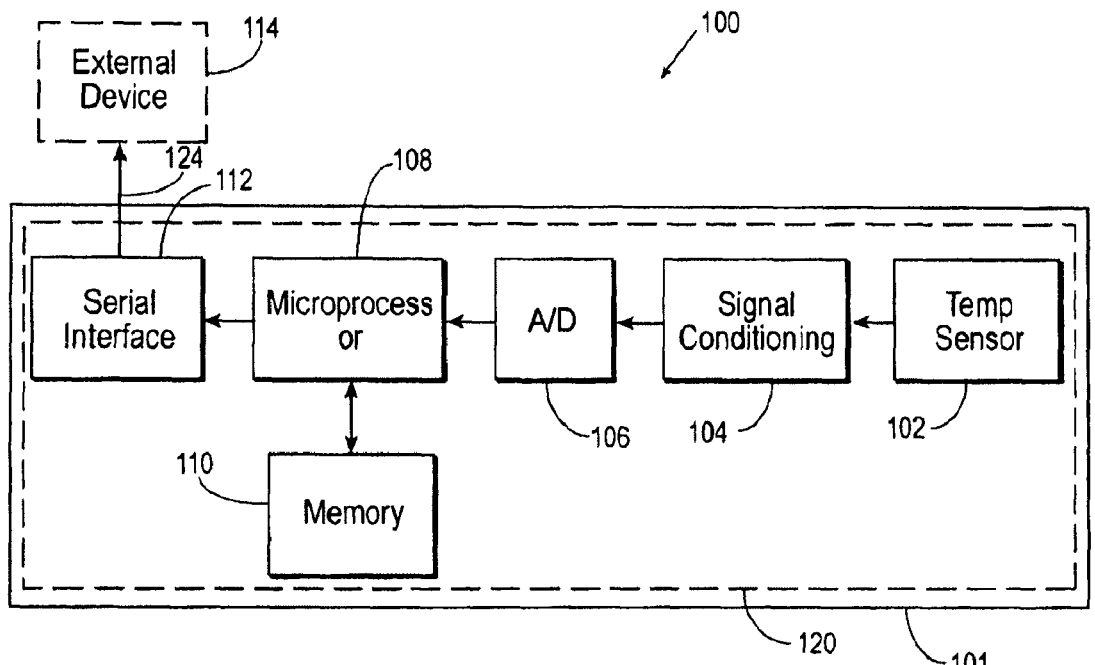
FIG. 2 is a schematic diagram showing the relationship of the logger components to an external device constructed in accordance with preferred embodiments of the present invention.

FIG. 2 is a schematic diagram showing a schematic diagram of a system 100 for logging and reading the temperature of the concrete mass of the preferred embodiment of the present invention. The system 100 includes a logger 120 enclosed in a housing such as a concrete mass. The logger 120 includes a temperature sensor 102 such as a thermistor that is responsive to temperature changes and sends an analog electrical signal to a signal conditioning device 104 such as an amplifier. After the signal is conditioned, the signal passes to an analog-to-digital (A/D) converter 106 to convert the conditioned analog signal to a digital signal.

The A/D converter 106 sends the digital signal to the microprocessor 108 for processing. When the microprocessor 108 receives the digital signal, the microprocessor 108 responds by performing an algorithm stored in the first memory device 110. According to this algorithm, a temperature value is first calculated from the data signal. Next, the value of the temperature is stored in the first memory device 110 for later use. Next, a maturity value is determined based on the temperature value and based on a maturity-temperature curve stored in the first memory device 110. Next, a mechanical strength value is determined from an empirical formula stored in the first memory device 110. The values of the maturity and mechanical strength are then stored in the first memory device 110. The microprocessor 108 then outputs the values of the temperature, maturity and mechanical strength as digital data to a serial interface 112. The serial interface 112 receives the digital data from the microprocessor 108 and transmits a signal to an external device 114 such as a reader.

The sensor 102, the signal conditioning device 104, the A/D converter 106, and the microprocessor 108 together form an inbound data transfer device for loading data into the first memory device. The serial interface 112 is one example of an outbound data transfer device.

Figure 3:
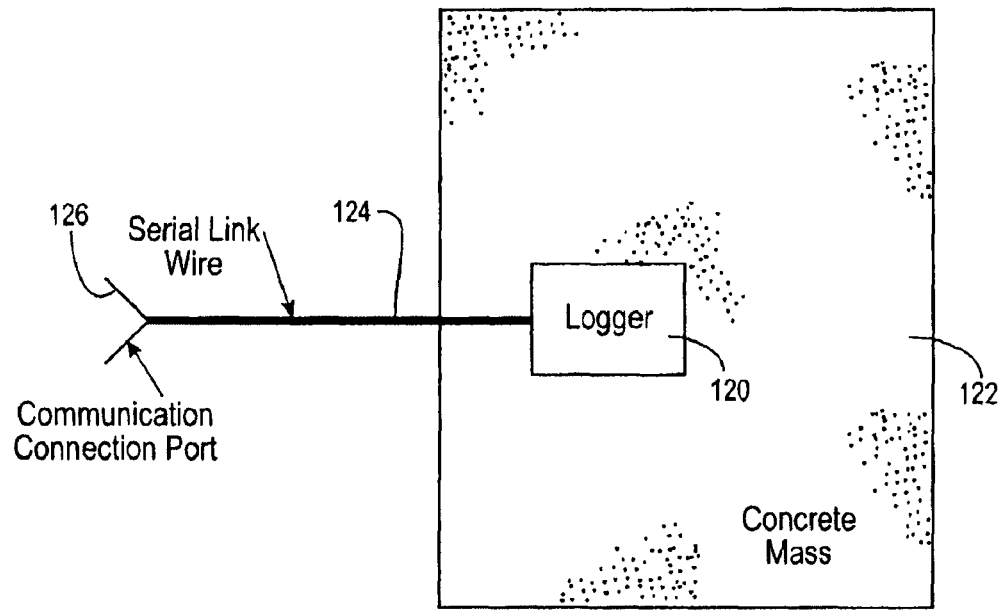
FIG. 3 is a schematic diagram of a logger embedded in a concrete mass and a communication wire, constructed in accordance with preferred embodiments of the present invention.

FIG. 3 is a schematic diagram showing the logger 120 embedded in a concrete mass 122. As can be seen by comparing FIG. 2 and FIG. 3, the logger 120 includes the temperature sensor 102, the signal conditioning device 104 such as an amplifier, the A/D converter 106, the microprocessor 108, the first memory device 110, and the serial interface 112. A communication wire 124, such as a serial link wire connects the logger 120 to a communication connection port 126.

The space containing the logger 120 within the concrete mass 122 is a tamper-resistant environment. The concrete mass 122 acts as a permanent anchoring apparatus for ensuring data are not removed from the tamper-resistant environment.

Figure 4:
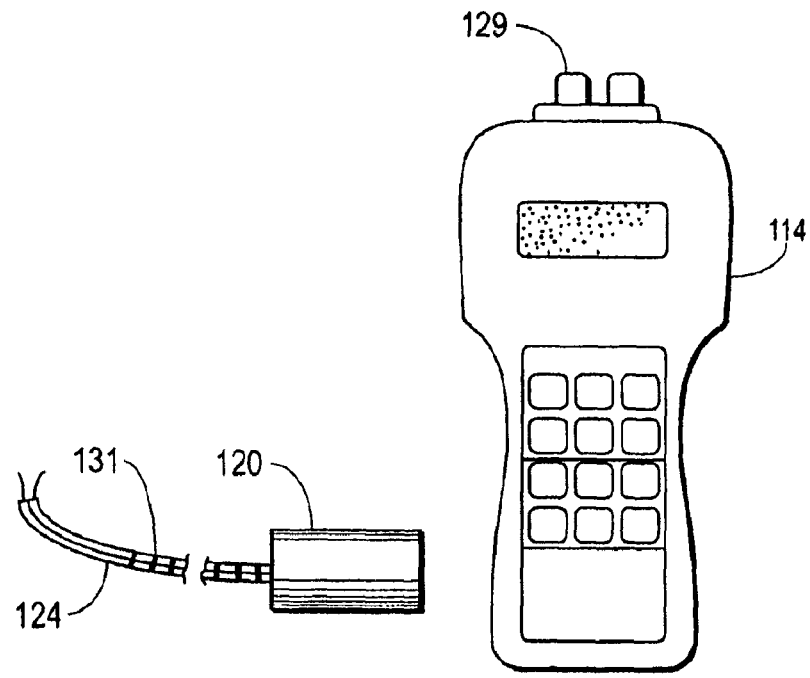
FIG. 4 is a handheld reader and a logger constructed in accordance with preferred embodiments of the present invention.

FIG. 4 is a plan view of the external device 114 and the logger 120. The external device 114 can be a reader 128. The communication wires 124 extend from the logger 120. The communication wires 130 have marks 131 to indicate the depth to which the logger 120 is embedded in the concrete mass 122. The reader 128 has receiving ports 129 that are color-coded to match colors of ends of the communication wires 130.

Figure 5:
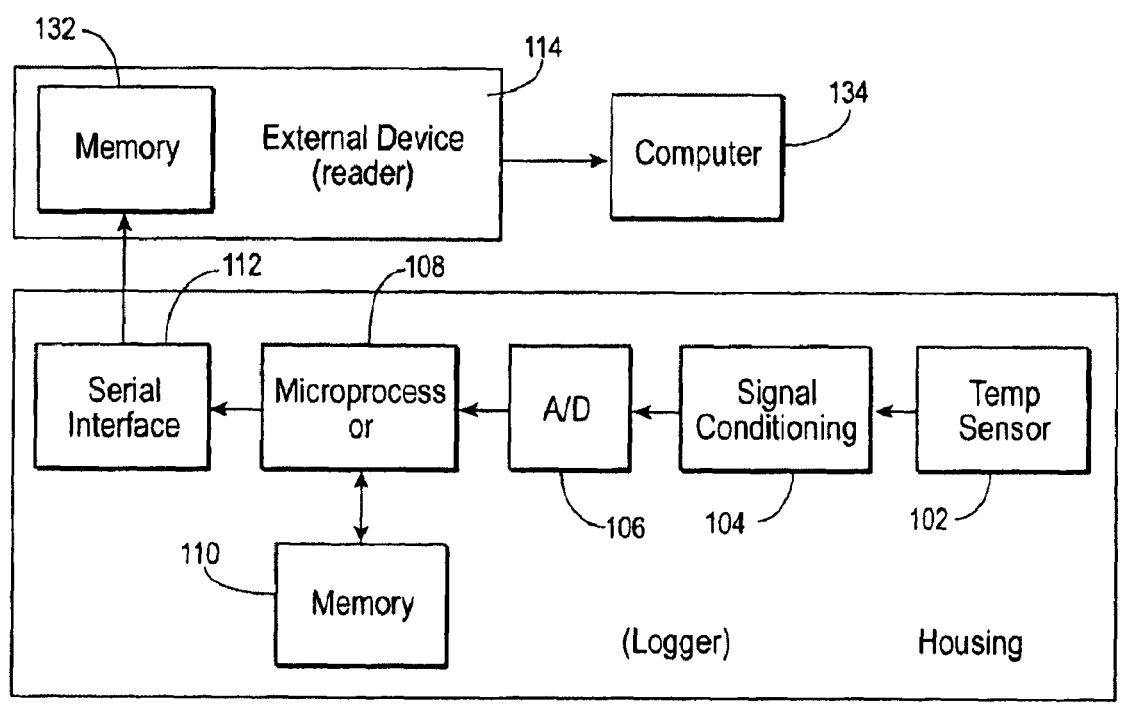
FIG. 5 is a schematic diagram showing a data path from a temperature sensor and an external computer.

FIG. 5 is a schematic diagram similar to FIG. 1. However, in FIG. 5, the external device 114 has a second memory device 132. The first and second memory devices 110 and 132 can be one or more of several memory devices, such as a random access memory device within a computer, flash memory or an electrically erasable programmable read-only memory (EEPROM). The external device 114 also sends the data it receives from the logger 120 to a second computer 134 (sometimes referred to herein as "computer"). The second computer 134 may serve as a backup for the mechanical data produced by the logger 120 in case of failure of the external device 114. The second computer 134 may also publish the data on a world-wide network of information-sharing computers (world-wide web).

Figure 6:
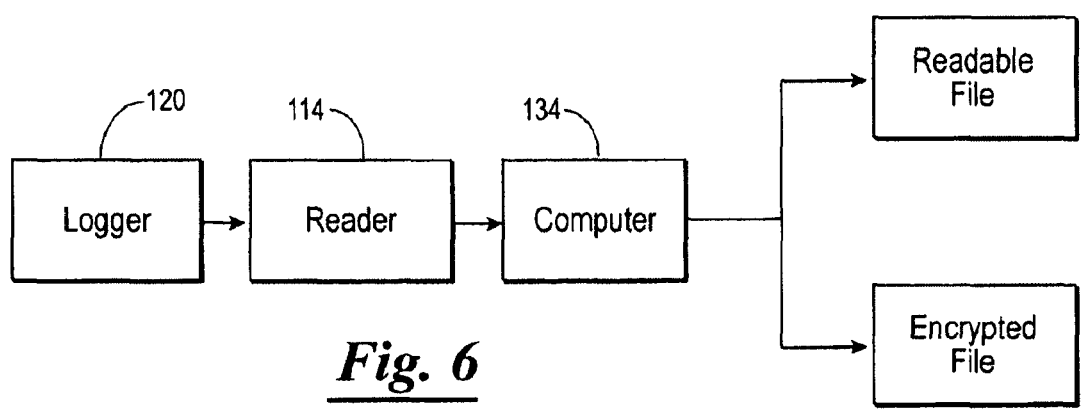
FIG. 6 is a schematic diagram showing a data path followed by readable files from the logger of the preferred embodiment of the present invention.

FIG. 6 shows a secure data file flow schematic diagram. As discussed above in the discussion section, the data is generated by the logger 120 as data files and are unalterable by the user. The reader 114 receives the data file and transmits it to the second computer 134. At the second computer 134, the data in the file is encoded or encrypted to render the data file unreadable and unalterable without a decoding key. The second computer 134 is programmed with the decoding key so that the data file can be read and/or transferred to third parties in either a readable form or an encrypted form.

Figure 7:
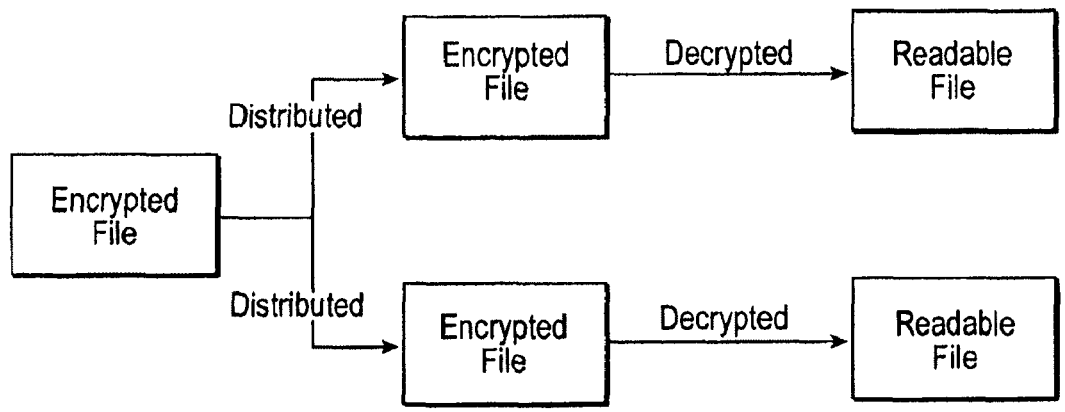
FIG. 7 is a schematic diagram showing dissemination of the secure data via encrypted files that are decrypted for viewing by the final intended recipient.

FIG. 7 shows that the encrypted files can be distributed to multiple users and then decrypted by the recipient to allow the final recipient to view the original data while being assured that the data have not been altered at any point along the way.

Figure 8A:
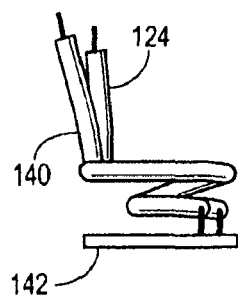
FIG. 8a is a side elevation view of a Z-bend communication wire connected to a serial interface of the logger of the preferred embodiment of the present invention.

FIGS. 8a-f shows various views of the logger 120 being assembled for use in the concrete mass. In FIG. 8a, the communication wire 124 is connected to a printed circuit board (PCB) 142 on which the microprocessor 108 and the first memory device 110 are mounted. The communication wire 124 is configured in a Z-bend to absorb high stress concentrations and thereby prevent damage to the bond between the encasement and the communication wire 124 beyond the first bend of the Z-bend configuration. From FIGS. 8A and 8b, one can see that the communication wire 124 is on a bottom side of the PCB 142 and a battery 144 is on a top of the PCB 142. This arrangement conserves space and preserves the orientation of the wire 124 during encasement operations.

Figure 8C:
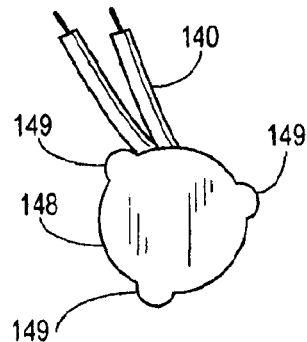
FIG. 8c is a bottom plan view of a mounting plate of the logger constructed in accordance with preferred embodiments of the present invention.
Figure 8E:
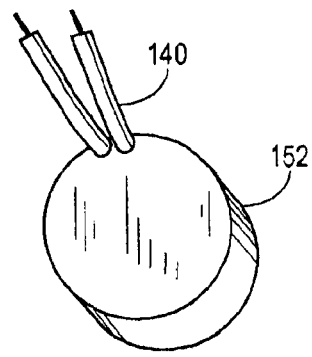
FIG. 8e is a perspective view of an inner case of the logger fitting inside a outer case of the logger.
Figure 8B:
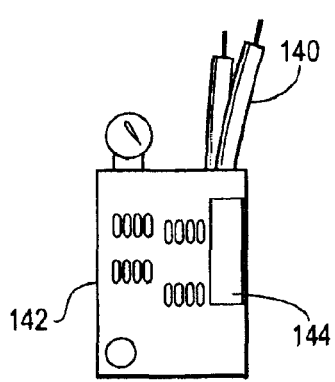
FIG. 8b is a bottom plan view of the communication wire and a printed circuit board (PCB) of FIG. 6A.
Figure 8D:
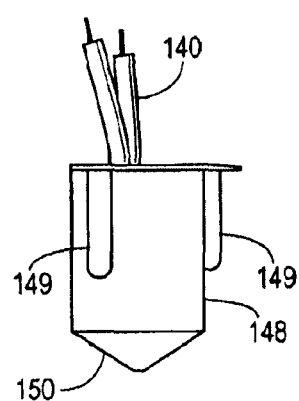
FIG. 8d is a side cut-away view of an inner case constructed in accordance with preferred embodiments of the present invention.
Figure 8F:
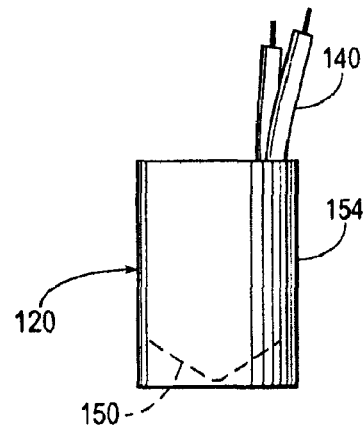
FIG. 8f is a perspective view of the outer case of the logger constructed in accordance with preferred embodiments of the present invention.
Figure 8G:
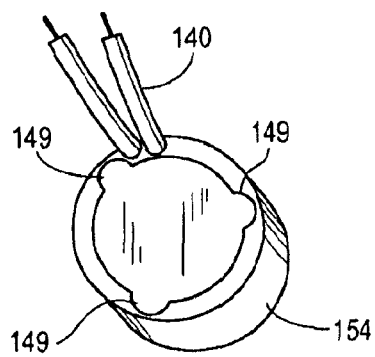
FIG. 8g is a side elevation view of the outer case of the logger attached to communication wires.

FIGS. 8c and 8d show a first stage of a preferred dual-stage hardened encasement for encasing the serial interface 112, microprocessor 108, the first memory device 110, A/D 106, signal conditioning 104 and temperature sensor 102 (collectively referred to as "components") of the logger 120. A first-stage encasement 148 is formed about the components, PCB 142 and batter 144 of the logger 120. The first state encasement 148 includes a plurality, such as three, tabs 149, and a conical, frusto-conical or pyramidal shaped bottom 150. No components, PCB 142 or battery 144 extend into any of the tabs 149 or the tip of the bottom 150 during the first-stage encasement process. In the second stage encasement, the first state encasement 148 is encased within a second encasement 154 such that the tabs 149 and the bottom 150 form the minimum outer boundaries of the second encasement 154. Both the first and second encasements 148 and 154 cooperate to constitute protective means for protecting the components, such as the first memory device 110 from exposure to damage. Although two encasements have been shown and described herein, it should be understood that additional encasements can be used.

The first and second encasements 148 and 154 can be formed of the same or different materials. The first and second encasements 148 and 154 can be formed from epoxy resin, polyester resin, or any other suitable materials having sufficient characteristic and sufficient thickness to protect the logger 120 components from effects of the medium and/or environment surrounding the logger 120. For an effective encasement, the combined thickness of the first and second encasements 148 and 154 must be adequate to shield electromagnetic interferences which can effectively "short out" the electrical signals within the logger 120 resulting from uncontrolled capacitive coupling. A conductive material, such as metal shavings or graphite, can be added to the material forming the second encasement 154 to provide additional electromagnetic shielding from the curing concrete.

The second encasement 154 is preferably color-coded or provided with other visual differentiation features for easy identification of logger types and versions. Each of several colors corresponds to the logger type and version.

The temperature sensor 102 is desirably located near the surface of the hardened encasement to minimize thermal lag times. This is important to provide accuracy to the temperature history.

Figure 9:
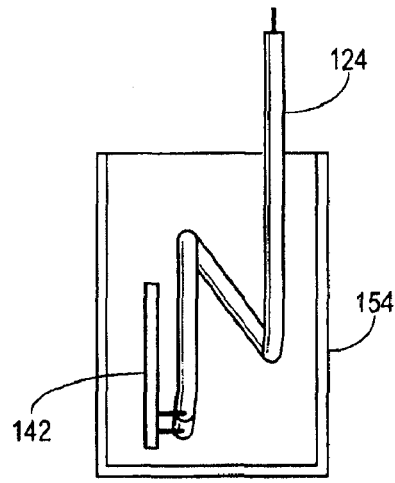
FIG. 9 is a side elevation view of a Z-bend communication wire connected to a serial interface of the logger of the preferred embodiment of the present invention.

FIG. 9 shows the PCB 142 encased in the logger encasement attached to the communication wire 124.

Figure 10A:
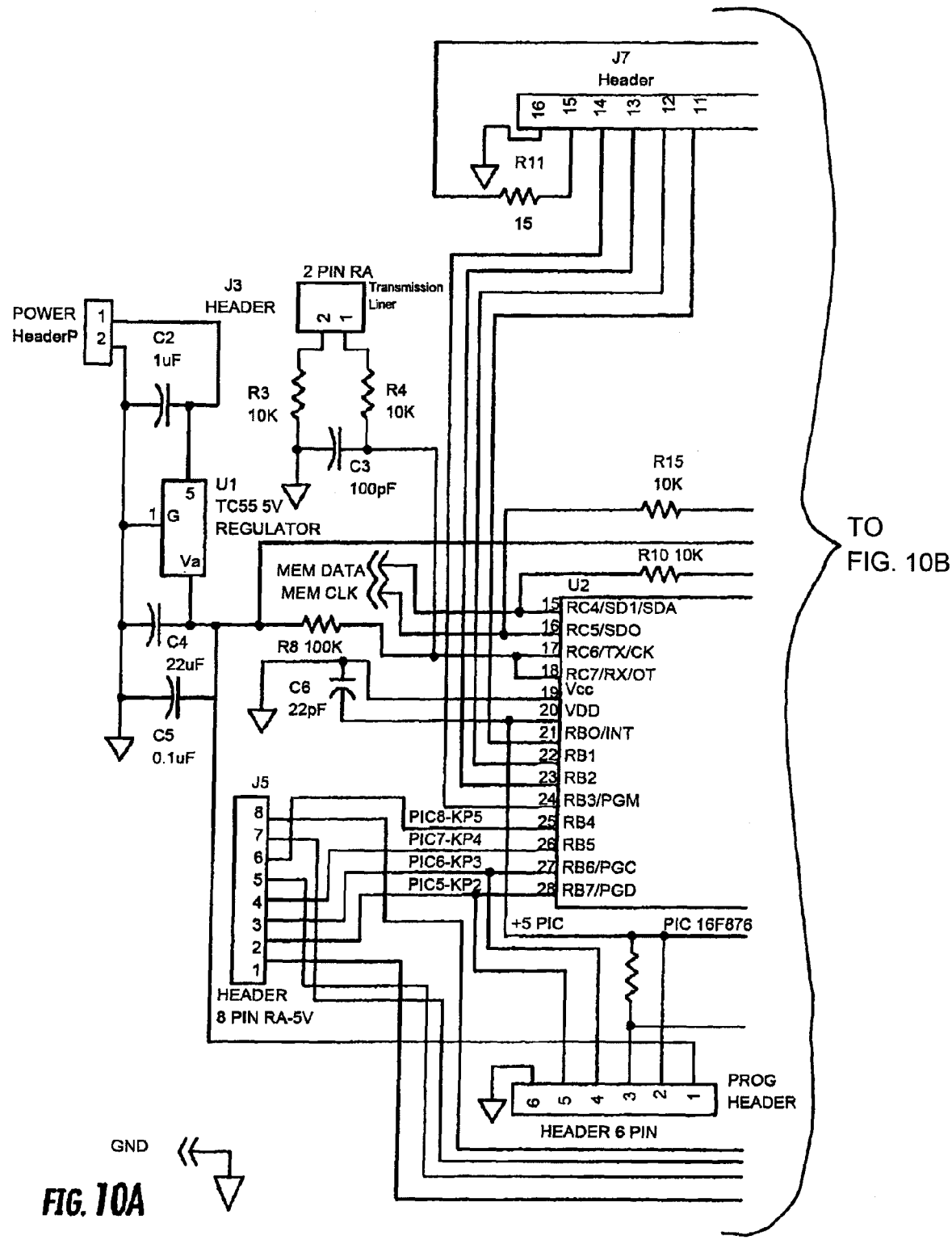
FIGS. 10A and 10B are an electrical schematic diagram of the reader.
Figure 10B:
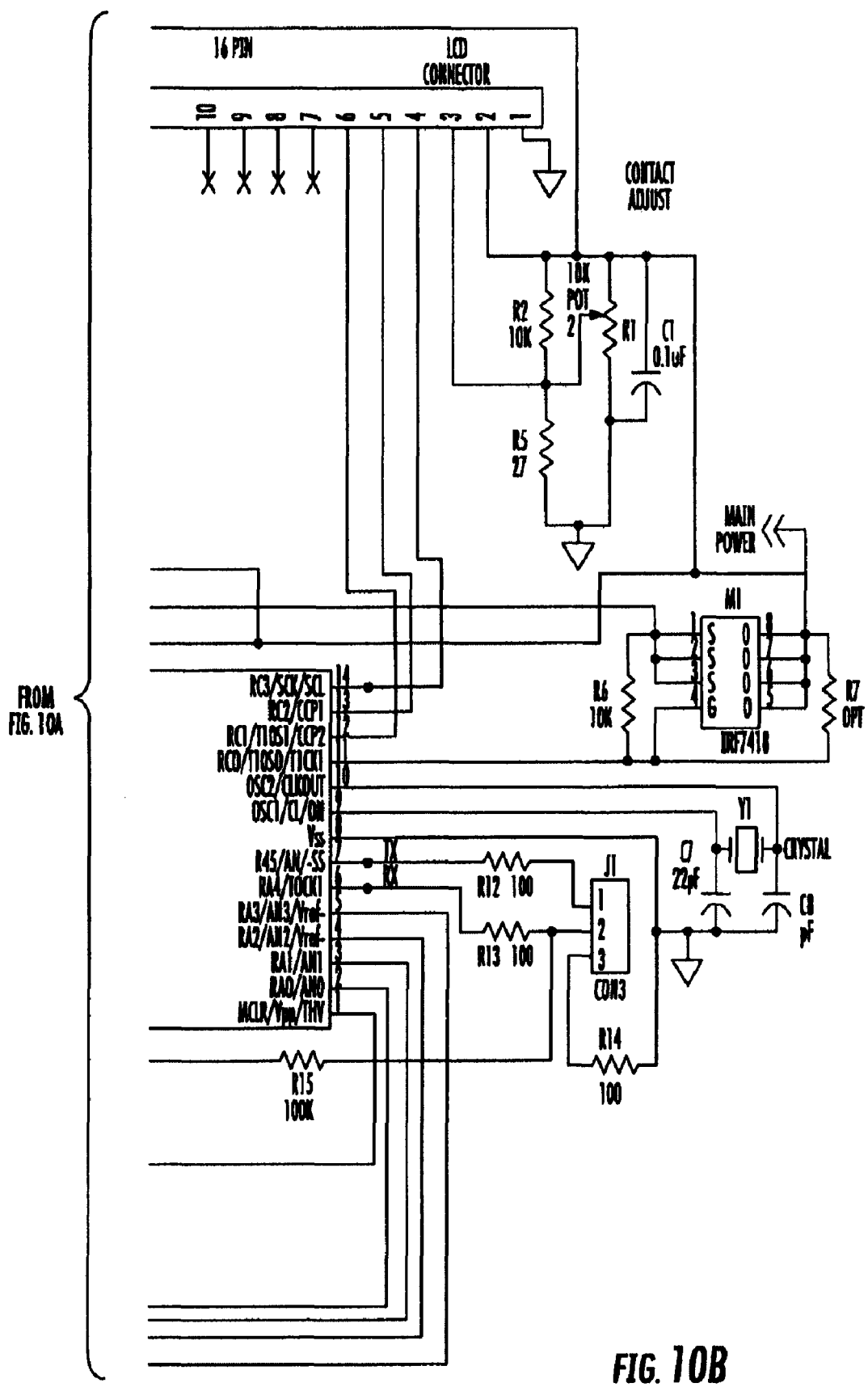

FIGS. 10A and 10B show an electrical schematic of the electrical circuit 160 for the reader.

Figure 10C:
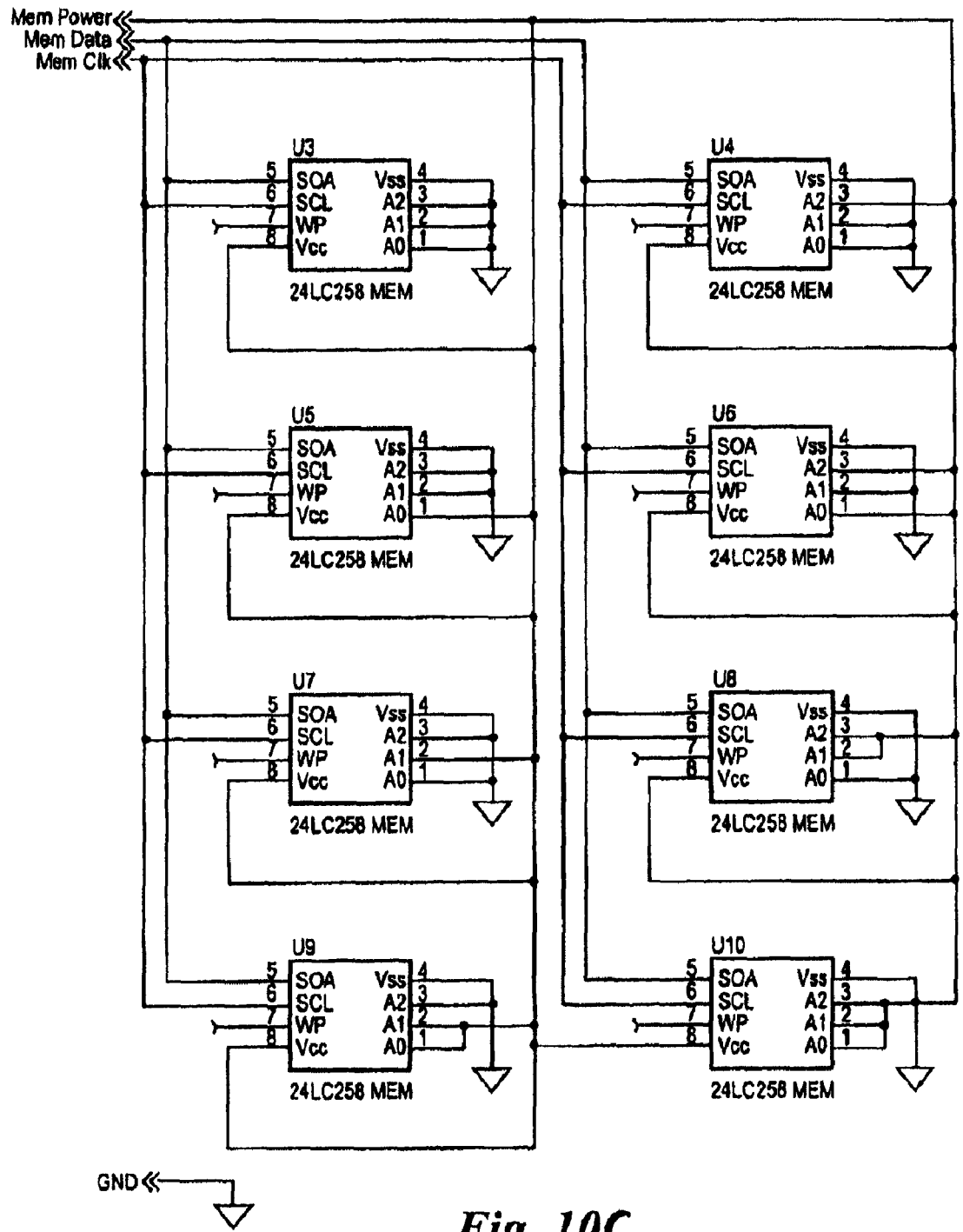
FIG. 10C is an electrical schematic diagram of a memory portion of the reader shown in FIGS. 10A and 10B.

FIG. 10C shows another electrical schematic of a portion 162 of the electrical circuit 160 for the reader. The portion 162 is the memory portion of the electrical circuit 160.

Figure 11:
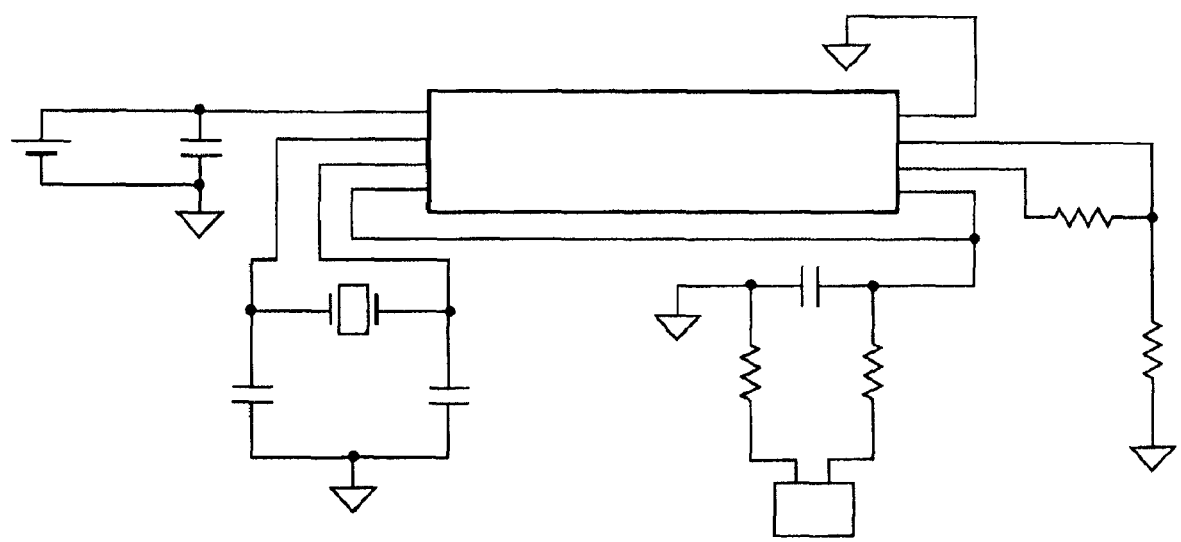
FIG. 11 is an electrical schematic diagram of the logger.

FIG. 11 shows an electrical schematic for an electrical circuit 170 in the logger 120.

Figure 12:
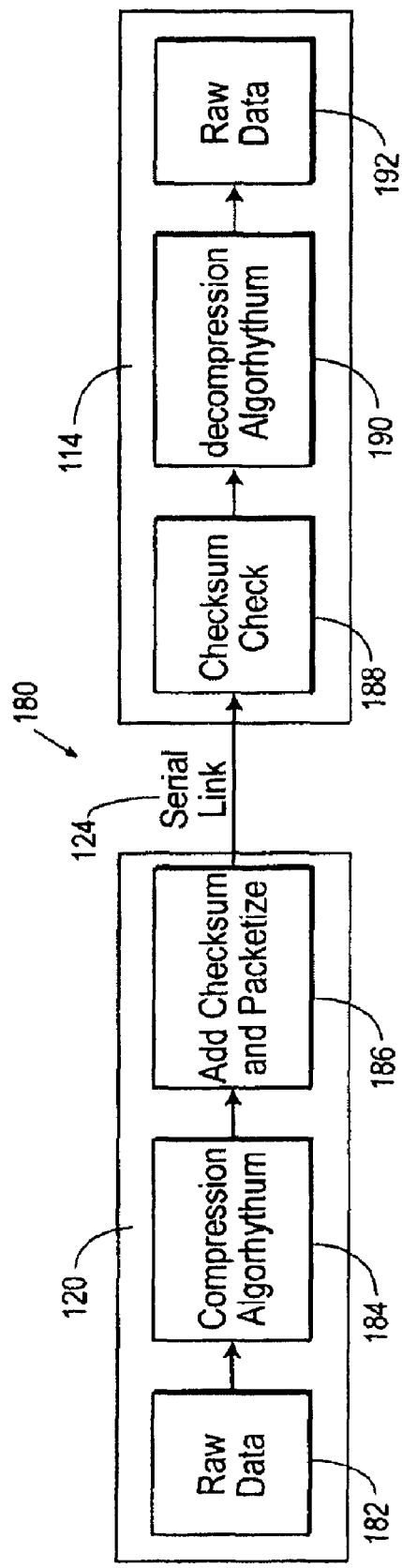
FIG. 12 is a schematic diagram illustrating an error checking protocol.

FIG. 12 shows a schematic diagram illustrating an error checking protocol 180 for the transmission of the mechanical data. At step 182, the raw (mechanical) data has already been produced by the logger 120. At step 184, the data is compressed by a suitable data compression algorithm. At step 186, the data is organized into groups of bytes called packets.

The packets have a one-byte CHECKSUM value. This CHECKSUM value is a simple addition of all of the bytes in the packet.

After step 186, the data packets are transmitted from the logger 120 to the reader 114 along the serial link 124. After the data arrives at the reader 114, at step 188 the CHECKSUM value is again calculated by adding up all the bytes in the packet. If the CHECKSUM value is not the same for the reader as it was for the logger 120, there has been a transmission error. If there has been no transmission error, the data is then decompressed by a decompression algorithm at step 190. At step 192, the method has produced raw data again and the method stops.

From the above description it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed is:

1. A system for providing secure, remote access to mechanical data associated with mechanical properties of a concrete mass, comprising:
    a logger associated with the concrete mass, comprising:
        at least one sensor adapted to measure physical properties of the concrete mass and generate sensor data indicative of the physical properties of the concrete mass;
        a microprocessor adapted to receive the sensor data and calculate mechanical data associated with the concrete mass; and
        an outbound data transfer device;
    a reader adapted to receive the mechanical data associated with the concrete mass from the outbound data transfer device of the logger; and
    a computer receiving the mechanical data from the reader and distributing the mechanical data to one or more users.

2. The system of claim 1, wherein the logger further comprises a memory device.

3. The system of claim 2, wherein the memory device stores the sensor data and mechanical data.

4. The system of claim 2, wherein the memory device stores non-sensor data that is selected from a group consisting of location information, a project identifier, time-related data, mix design information, datum temperature, activation energy and a threshold value.

5. The system of claim 1, wherein the physical properties measured by the at least one sensor is are selected from a group consisting of temperature, moisture, relative humidity, electrical conductivity, thermal conductivity, alkalinity, oxidation-reduction potential and sonic velocity.

6. The system of claim 1, wherein the logger further includes a time-keeping device to track the time between the measurements of the physical properties.

7. The system of claim 1, wherein the mechanical data is transferred from the outbound data transfer device to the reader via a first transfer protocol.

8. The system of claim 7, wherein the first transfer protocol is encrypted.

9. The system of claim 7, wherein the mechanical data is transferred in an unalterable form.

10. The system of claim 1, wherein the mechanical data is transferred from the reader to the computer via a second transfer protocol.

11. The system of claim 10, wherein the second transfer protocol is encrypted.

12. The system of claim 10, wherein the mechanical data is transferred in an unalterable form.

13. The system of claim 1, wherein the computer distributes the mechanical data to one or more users via a world-wide network.

14. The system of claim 13, wherein the world-wide network is the Internet.

15. The system of claim 13, wherein the world-wide network includes the World Wide Web.

16. The system of claim 1, wherein the one or more users includes one or more third parties.

17. A system for providing secure, remote access to mechanical data associated with mechanical properties of a concrete mass, comprising:
    one or more secondary loggers associated with the concrete mass and including at least one sensor adapted to measure physical properties of the concrete mass and generate sensor data indicative of the physical properties of the concrete mass;
    a central receiving logger associated with the concrete mass, comprising:
        at least one sensor adapted to measure physical properties of the concrete mass and generate sensor data indicative of the physical properties of the concrete mass;
        a microprocessor adapted to receive the sensor data from the one or more secondary loggers and the central receiving logger and calculate the mechanical data associated with the concrete mass; and
        an outbound data transfer device;
    a reader adapted to receive the mechanical data associated with the concrete mass from the outbound data transfer device of the central receiving logger; and
    a computer receiving the mechanical data from the reader and distributing the mechanical data to one or more users.

18. The system of claim 17, wherein the central receiving logger further comprises a memory device.

19. The system of claim 18, wherein the memory device stores the sensor data from the one or more secondary loggers and the central receiving logger and the mechanical data.

20. The system of claim 18, wherein the memory device stores non-sensor data that is selected from a group consisting of location information, a project identifier, time-related data, mix design information, datum temperature, activation energy and a threshold value.

21. The system of claim 17, wherein the physical properties measured by the at least one sensor is of the at least one secondary logger and the central receiving logger are selected from a group consisting of temperature, moisture, relative humidity, electrical conductivity, thermal conductivity, alkalinity, oxidation-reduction potential and sonic velocity.

22. The system of claim 17, wherein the central receiving logger further includes a time-keeping device to track the time between the measurements of the physical properties.

23. The system of claim 17, wherein the computer distributes the mechanical data to one or more users via a world-wide network.

24. The system of claim 23, wherein the world-wide network is the Internet.

25. The system of claim 23, wherein the world-wide network includes the World Wide Web.

26. The system of claim 17, wherein the one or more users includes one or more third parties.

27. A method for providing secure, remote access to mechanical data associated with mechanical properties of a concrete mass, comprising the steps of:
- associating a logger with the concrete mass, the logger including at least one sensor;
- generating, via the sensor, sensor data indicative of the physical properties of the concrete mass;
- calculating, via a microprocessor, mechanical data associated with the concrete mass from the sensor data;
- providing the mechanical data associated with the concrete mass to a reader;
- providing the mechanical data to a computer; and
- distributing, via the computer, the mechanical data associated with the concrete mass to at least one user.

28. The method of claim 27, wherein in the step of distributing, the mechanical data is distributed to at least one user via a world-wide network of information sharing computers.

29. The method of claim 27, wherein in the step of distributing, the mechanical data is distributed to at least one user via the Internet.

30. The method of claim 27, wherein in the step of distributing, the mechanical data is distributed to at least one user using the World-Wide Web.

* * * * *